United States Patent [19]

Jowitt et al.

[11] Patent Number: 4,598,577

[45] Date of Patent: Jul. 8, 1986

[54] ANALYSIS OF MATERIALS

[75] Inventors: Raymond Jowitt, Guisborough; Ian D. Abell, Saltburn-by-the-Sea, both of England

[73] Assignee: British Steel Corporation, London, England

[21] Appl. No.: 639,592

[22] Filed: Aug. 10, 1984

[30] Foreign Application Priority Data

Aug. 24, 1983 [GB] United Kingdom ............... 8322709

[51] Int. Cl.$^4$ ............................................. G01N 21/73
[52] U.S. Cl. ............................................ 73/23; 356/36
[58] Field of Search ............... 73/23, 28, 19; 250/343; 356/36, 316, 318; 266/80, 44, 99; 75/60, 28, 20 R

[56] References Cited

U.S. PATENT DOCUMENTS 4,220,414  9/1980  Barringer ............................. 356/36
4,468,009  8/1984  Clauss et al. ......................... 266/99

FOREIGN PATENT DOCUMENTS 0059146  4/1982  Japan .................................. 356/36
0059147  4/1982  Japan .................................. 356/36
0059148  4/1982  Japan .................................. 356/36

Primary Examiner—Stephen A. Kreitman
Attorney, Agent, or Firm—Kinney & Lange

[57] ABSTRACT

This invention provides a method of analyzing materials, comprising the steps of subjecting a surface of the material to high energy impact by a laser to cause ablation and vaporization such as to generate a gaseous and/or gas-born sample of the material, transporting all or part of the gaseous and/or gas-born sample of the material to a remote analytical apparatus, and analyzing the gaseous and/or gas-born sample of the material at the remote analytical device so as to determine the constituent compartments of the material, together with Apparatus for carrying out this method.

7 Claims, 4 Drawing Figures

ANALYSIS OF MATERIALS

BACKGROUND OF THE INVENTION

This invention relates to the analysis of materials.

More particularly, although nor exclusively, the invention relates to the analysis of iron or steel, together with the associated slag during iron or steel making, or in primary or secondary steel processing. An object of the invention is to provide a method of and apparatus for such analysis capable of convenient and simple and rapid usage.

SUMMARY OF THE INVENTION

According to one aspect of the invention there is provided a method of analysing materials, comprising the steps of subjecting a surface of the material to high energy impact by laser to cause ablation and vapourisation such as to generate a gaseous and/or gas-borne sample of the material, transporting all or part of the gaseous and/or gas-borne sample of the material to a remote analytical apparatus, and analysing the gaseous and/or gas-borne sample of the material at the remote analytical device so as to determine the constituent components of the material.

According to another aspect of the present invention, there is provided apparatus for the analysis of materials comprising laser generating means for producing a gaseous and/or gas-borne sample from a surface of the material, means for transporting the so produced sample to a remote analytical device for determining the constituents of the material.

The surface of the material to be subjected to testing may be a natural surface or may be a specially obtained, exposed, and/or prepared surface. The surface may be liquid, solid or powder.

It is to be appreciated that the energy density at the surface of the materials needs to be sufficiently high to generate a gaseous and/or gas-borne (aerosol type) sample of the material which provides a true representation of the composition of the material being analysed. Thus, for example there should be minimal preferential vapourisation of constituent elements. For this reason ablation and vapourisation of the surface of the material is by means of the rapid input of high energy by means of a laser directed at the surface of the material. The laser may be operated in the form of a pulse, or in the form of a timed series of pulses.

The aerosol sample of the material may be transported to the analytical device by means of an inert gas (such as argon).

The analytical device may comprise an excitation unit and a spectrometer for measurement of the resultant optical emissions. Thus excitation may be by any of the known optical emission sources, the use of an inductively coupled plasma often being particularly convenient.

BRIEF DESCRIPTION OF THE DRAWINGS

In order that the invention may be more readily understood one embodiment thereof will now be described by way of example with reference to the accompanying drawing in which.

DETAILED DESCRIPTION OF THE PREFERRED EMBODIMENTS

Figure 1:
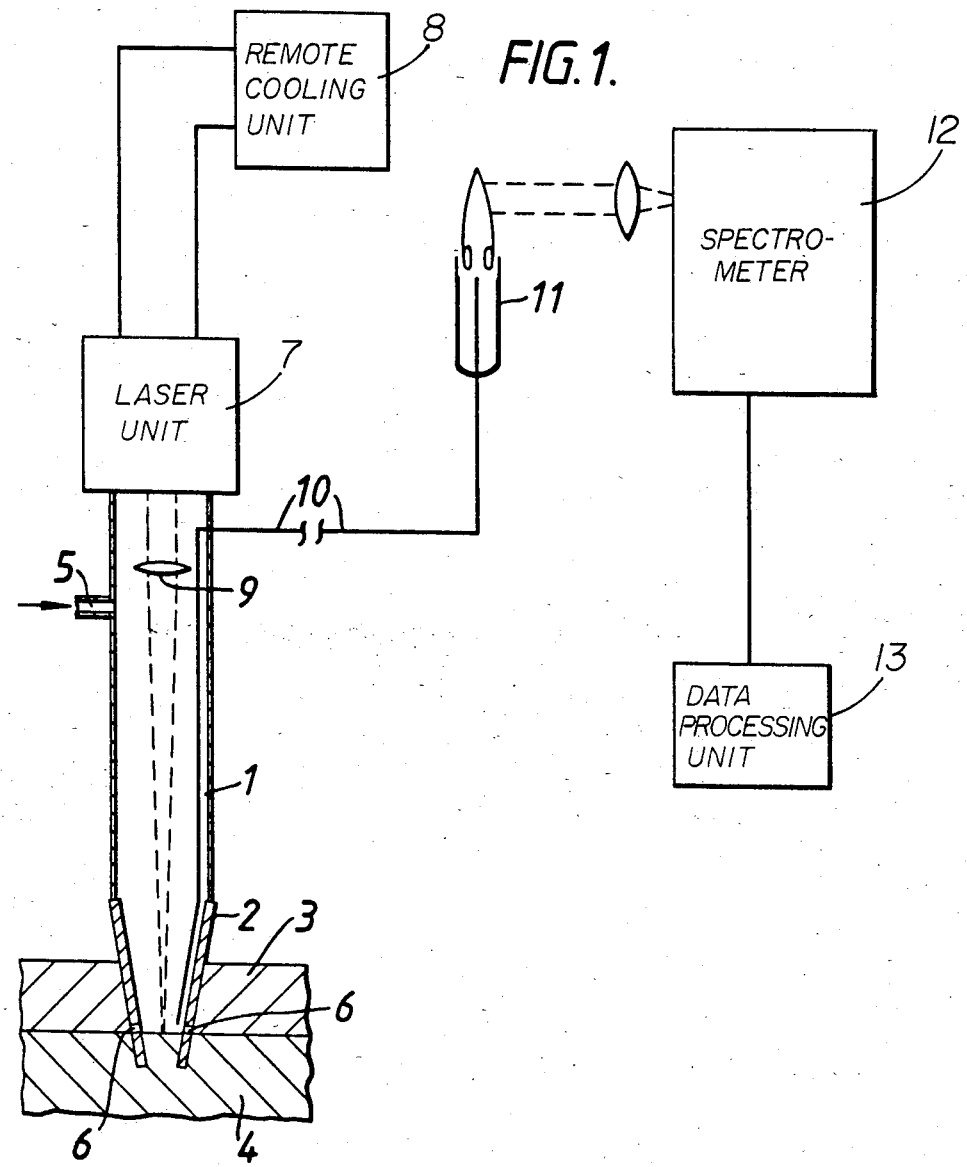
FIG. 1 shows, in diagrammatic form, apparatus for analysing molten metal such as steel, in a containing vessel.

As can be seen in FIG. 1 a probe 1 having a refractory end 2 is located within a molten metal containing vessel (not shown) so as to penetrate the slag layer 3 over the molten metal and reach and expose a surface of the metal 4. Ingress of molten metal into the refractory end of the probe 1 is minimised by pressurising the probe by means of a flow of inert gas (usually argon) entering the probe at port 5 and exciting the probe at restricted ports 6.

Laser pulses are generated by laser rods, flash lamps, and possibly a "Q switch" mounted in a unit 7 disposed at the upper end of the probe 1. It is to be observed that the components of unit 7 are cooled by means of an appropriate coolant fluid or fluids cycled therethrough from a remote unit 8 which also supplies power to unit 7.

A lens 9 is disposed within the probe 1 and focuses the laser pulses onto the surface of the metal exposed at the end of the refractory tip of the probe. The interaction of the laser pulses and the surface of the metal produces an aerosol carrying a complete cross-section of the constitution of the metal. The aerosol so generated is transmitted via a tube 10 from the surface of the metal to an inductively coupled plasma torch 11. The characteristic radiations from the plasma are dispersed, detected and quantified by a spectrometer 12, the analogue outputs of which are converted to element compositions by a data processing unit 13.

It will be appreciated that the probe may be raised in height slightly so that it terminates in and exposes a surface of the slag layer, if analysis is required.

In an alternative arrangement (not illustrated) a probe may be immersed so as to sample a quantity of molten metal from the containing vessel. Laser pulses may then be focused on the still liquid, solidifying or solidified sample, producing a sample aerosol which may be transported to an analytical device. In this form the end of the probe may be disposable and be changed between analyses, and the analysis may be performed with the probe in situ, during retraction, or when retracted.

Figure 2:
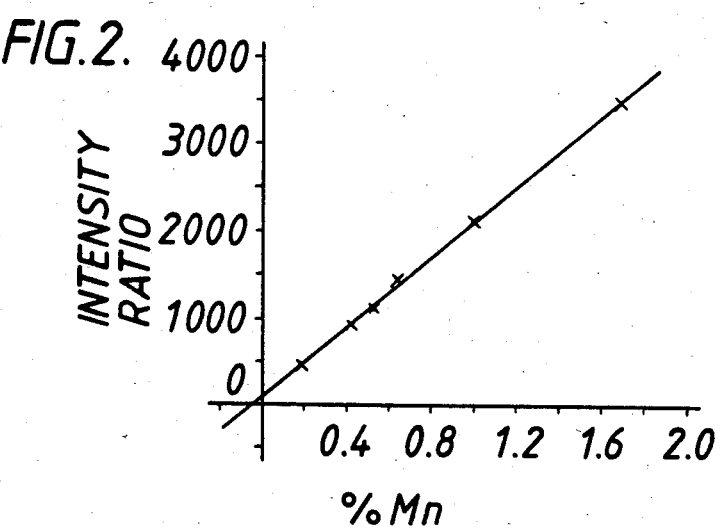
FIGS. 2, 3 and 4 show calibration graphs for Manganese, Nickel and Chromium respectively.
Figure 3:
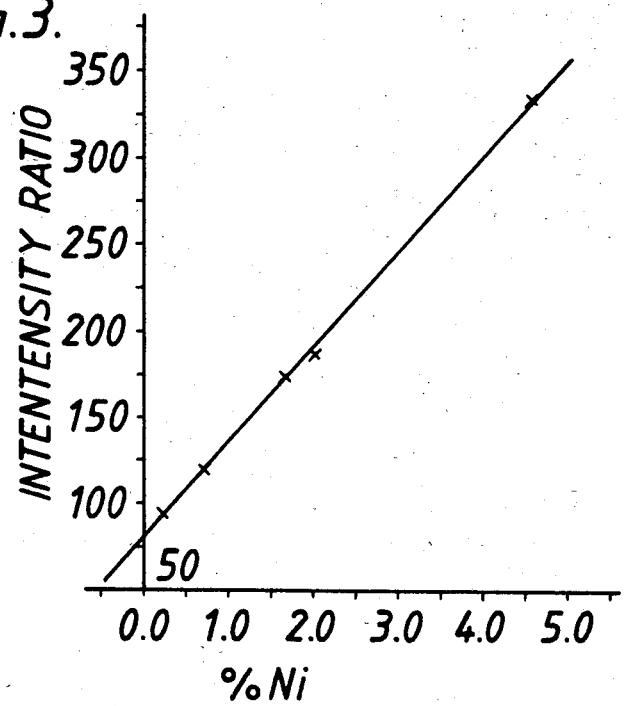
Figure 4:
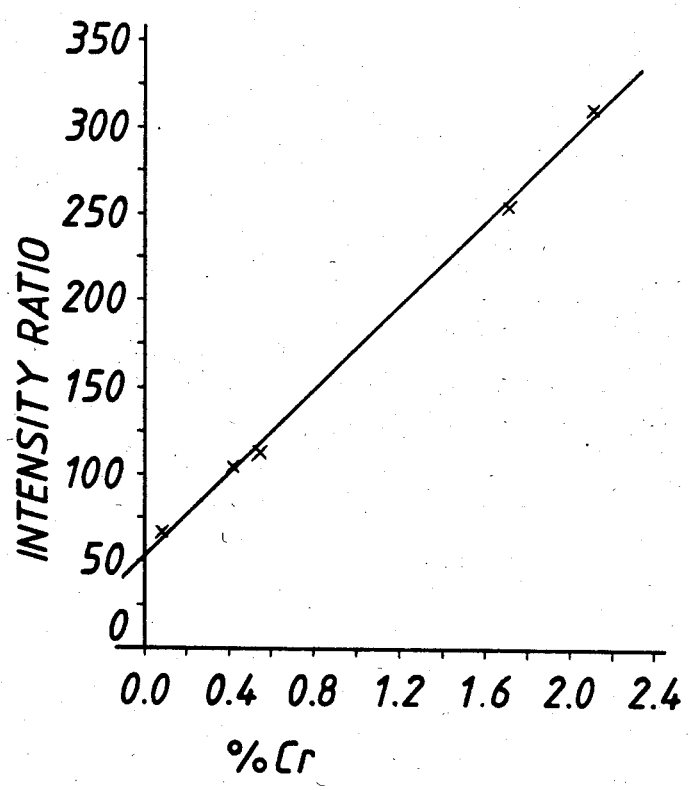

We have found that it is possible for laser generated aerosols of the kind herein described to be transported 80 meters to the plasma torch unit in approximately 10 seconds. Optical emission analysis of the plasma flame has provided the calibrations illustrated in FIGS. 2, 3 and 4 for Manganese, Nickel and Chromium respectively. It is to be noted that the expression "Intensity ratio" mentioned in the graphs in the intensity of the relevant element divided by the intensity of iron.

In another alternative arrangement (not illustrated) provision may be made for directing the laser pulses down the aerosol extraction tube for the aerosol (equivalent to tube 10) in order to ensure that the aerosol extraction is as close as possible to the point of aerosol generation. Desirably with such a design care would be taken to ensure that all of the aerosol sample produced by one laser pulse is removed from the laser path prior to the occurrence of the next pulse so as to avoid any energy absorption by the remnant aerosol.

The invention has been described hereinabove in relation to the analysis of steel, to which it is pre-eminently suited, it is applicable to many other metals and other materials. Thus by way of example the invention can be applied to the analysis of an aluminium melt, or of a glass.

We claim:

1. A method of analysing metals during production or processing thereof, comprising the steps of subjecting a surface of the metal undergoing production or processing to high energy impact by a laser to cause ablation and vapourisation such as to generate a gaseous and/or gas-borne sample comprising a complete representation of the metal, transporting all or part of the gaseous and/or gas-borne sample of the metal to a remote analytical apparatus comprising an excitation unit and a spectrometer, and analysing the gaseous and/or gas-borne sample of the metal at the remote analytical apparatus so as to determine the constituent components of the metal.

2. Apparatus for the analysis of molten metal during production or processing thereof, comprising laser generating means for creating a gaseous and/or gas-borne sample from a surface of the metal undergoing the production of processing, an analytical device comprising an excitation unit and a spectrometer for determining the constituents of the metal located at a remote site, and a probe for contacting, obtaining and exposing a surface of the metal from the melt thereof, said probe including passages for the transmission of energy from the laser generating means for creating the gaseous and/or gas-borne sample from the surface, and for the transport of such sample to the remote analytical device.

3. A method of analyzing molten metal during production or processing thereof comprising the steps of contacting, obtaining and exposing a surface of the metal from the melt thereof to high energy impact by a laser to cause ablation and vapourization such as to generate a gaseous and/or gas-borne sample comprising a complete representation of the metal, transporting all or part of the gaseous and/or gas-borne sample of the metal to a remote analytical apparatus, and analyzing the gaseous and/or gas-borne sample of the metal at the remote analytical device so as to determine the constituent components of the metal.

4. A method in claim 3 wherein the laser is operated in the form of a timed series of pulses.

5. A method as claimed in claim 3 wherein the surface of the metal is a naturally arising surface.

6. A method as claimed in claim 3 wherein the surface of the metal is a specially obtained or exposed or prepared surface.

7. A method as claimed in claim 3 wherein the sample is transported to the analytical device by means of an inert gas.

* * * * *